United States Patent [19]

Flodin et al.

[11] 4,234,565
[45] Nov. 18, 1980

[54] POLYMER

[75] Inventors: Per G. M. Flodin, Täby; Peter G. Komlos, Märsta; Bengt G. Rånby, Djursholm, all of Sweden

[73] Assignee: Astra Chemical Products AB, Sodertalje, Sweden

[21] Appl. No.: 16,815

[22] Filed: Mar. 2, 1979

Related U.S. Application Data

[62] Division of Ser. No. 892,869, Apr. 3, 1978.

[30] Foreign Application Priority Data

Apr. 4, 1977 [SE] Sweden ........................ 7703901

[51] Int. Cl.$^3$ .............................................. A61K 9/32
[52] U.S. Cl. .......................................... 424/33; 424/81
[58] Field of Search ............................ 424/32, 33, 81; 526/260

[56] References Cited

U.S. PATENT DOCUMENTS

| | | | |
|---|---|---|---|
| 2,138,763 | 11/1938 | Graves | 526/260 |
| 3,651,029 | 3/1972 | Fujimoto et al. | 526/260 |
| 3,829,564 | 8/1974 | Merry et al. | 424/32 |

Primary Examiner—Shep K. Rose
Attorney, Agent, or Firm—Brumbaugh, Graves, Donohue & Raymond

[57] ABSTRACT

The present invention relates to polymers which have pH-depending solubility characteristics in aqueous solutions, whereby the polymers are copolymers between (a) methylmethacrylate (b) at least a monomer of the formula III

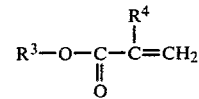

wherein $R^3$ is an alkyl group having 4 to 18 carbon atoms and $R^4$ is hydrogen or methyl; and (c) a monomer of the formula I

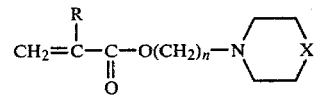

wherein R is hydrogen or methyl, n is an integer of from 1 to 4, and X is $=CH_2$ or $=O$; and/or a monomer of the formula II

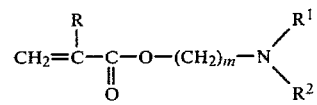

wherein R is hydrogen or methyl, $R^1$ and $R^2$ are each hydrogen, methyl, ethyl, propyl, isopropyl, isobutyl, t-butyl or n-butyl, and m is an integer of from 1 to 4, as well as a process for their preparation, and a product in the form of particles which have been coated with such a polymer, whereby the product is protected against dissolution at pH above 5, but shall be dissolved at pH below 4, the product preferably being one which is administered to ruminants in order to obtain rumen-bypass.

15 Claims, No Drawings

POLYMER

This application is a division of U.S. application Ser. No. 892,869 filed Apr. 3, 1978.

The present invention relates to a new polymer for filmcoating of feedstuffs, food and drugs, to a process for its preparation, as well as products coated with such a polymer.

The object of the present invention is to obtain a polymer by means of which feedstuffs, food and drugs can be filmcoated, whereby the polymer is not soluble or not soluble to any greater extent at pH above 5 while it is completely or almost completely soluble at pH below 3.

Within the feedstuff industry it is of interest in the manufacture of feedstuffs intended for ruminants to coat certain feedstuffs with a film coating in order to prevent release of the feedstuff in the rumen (the pH of which is about 5–6.5) and thereby prevent an attack from the microorganisms of the rumen on the feedstuff. Feedstuffs which are of interest to be coated are sugar, protein, amino acids, unsaturated fatty acids. On the other hand it is required that the feedstuff is released in the rennet stomach the pH of which is about 2, so that the animal to which it has been administered can use it.

It has thus previously been proposed to treat proteins, intended as feedstuffs, with formaldehyde, whereby formaldehyde creates cross links with the protein, or to coat with a polymer or a copolymer of a basic vinyl monomer or a basic amino acrylate or amino methacrylate monomer, whereby the feedstuff has been coated with the polymer or the copolymer.

It has thus previously been proposed coating of feedstuff products using cellulosepropionate-3-morpholinobutyrate as well. It has, however, been shown that the cellulose derivative has too high a permeability for water at pH 5 in order to give a practically useable product, i.e. a product which is not attacked by the rumen microorganisms.

It is also of interest to reduce the water permeability of a polymer which is used, in order to eliminate swelling of the coated product depending on the penetration of the water.

It has now been shown to be surprisingly possible to solve these problems applying the present invention which is characterized by a copolymerisate between
(a) methylmethacrylate
(b) at least one monomer of the general formula III

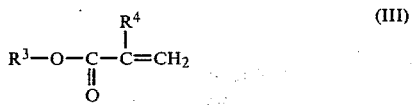

wherein $R^3$ is a straight or branched alkyl group having 4–18 carbon atoms, and $R^4$ is hydrogen or methyl; and
(c) a monomer of the general formula I

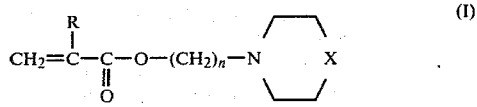

wherein R is selected from the group consisting of hydrogen and methyl, X is selected from the group consisting of =O and =CH$_2$, and n is an integer of from 1–4, preferably from 2–3, and/or a monomer of the general formula II

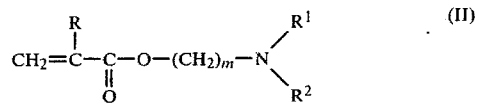

wherein R has the meaning given above, $R^1$ and $R^2$ are selected from the group consisting of hydrogen, methyl, ethyl, propyl, isopropyl, isobutyl, t-butyl, and n-butyl, whereby $R^1$ and $R^2$ are not both hydrogen and m is an integer 1–4, preferably 2–3.

The nitrogen contents of the polymer shall be 2.5–3.3%, preferably 2.7–3.1%.

The polymer shall have a softening temperature which is at least 25° C., preferably at least 39° C.

Further, the polymer shall have a molecular weight expressed as Mn (number average) determined against a polystyrene standard of 5,000–170,000, preferably at least 25,000, and a molecular weight expressed as Mw (weight average) of preferably at least 50,000.

The water steam permeability $Q_{40}$ shall be at most 1,600 g.mil/m$^2$.24 hours, (1 mil=0.001 inches=0.025 mm) preferably less than 1,000 g.mil/m$^2$.24 hours.

The monomer of formula III above present in the polymer has the task of reducing the water steam permeability of the polymer by creating a water repellent surface. Monomers within the definition of formula III above are butylmethacrylate, hexylacrylate, heptylacrylate, octylacrylate, cyclohexylacrylate, 2-ethylhexylacrylate, decylmethacrylate, dodecylmethacrylate, tridecylmethacrylate, stearylmethacrylate. Preferred monomers are i.a. butylmethacrylate and stearylmethacrylate.

Stearylmethacrylate and/or butylmethacrylate are present in the monomer in an amount which is at least 0.5 mol-%, preferably 1–6 mol-% of the amount of charged monomers, when a monomer of formula I is present, and in an amount of at least 0.5 mol-%, preferably 1–10 mol-% of the amount of charged monomers when a monomer of formula II is present.

A nitrogen content of 2.5% corresponds to a content of 2-(4-morpholino)ethylacrylate of about 22 mol-% of the final polymer and a nitrogen content of 3.3% corresponds to a content of said monomer of about 31 mol-% of the final polymer, when 1 mol-% stearylmethacrylate is present.

A nitrogen content of 2.5% corresponds to a content of 2-(N,N-dimethylamino)ethylmethacrylate of about 21 mol-% in the final polymer and a nitrogen content of 3.3% corresponds to a content of said monomer of about 30 mol-% in the final polymer, when 1 mol-% stearylmethacrylate is present.

In those cases where different reaction rates of the monomers present are at hand it is necessary to have an excess, especially of the monomer of formula I, at the preparation. Thus a monomer of formula I is charged in an amount of 30–50 mol-%, preferably 35–45 mol-% and a monomer of formula II usually in an amount of 20–30 mol-%, preferably 22–28 mol-%.

According to a preferred embodiment of the invention the copolymer consists of
(a) methylmethacrylate
(b) stearylmethacrylate, and
(c) 2-(4-morpholino)ethylacrylate whereby the amount of (b) is 1 mol-% and the amount of (c) is 35–45 mol-% of the amount of charged monomers.

According to another preferred embodiment of the invention the copolymer consists of
(a) methylmethacrylate
(b) stearylmethacrylate, and
(c) 2-(4-morpholino)ethylmethacrylate
whereby the amount of (b) is at least 1 mol-% and the amount of (c) is 22–28 mol-% of the amount of charged monomers.

According to a further another preferred embodiment of the invention the copolymer consists of
(a) methylmethacrylate
(b) stearylmethacrylate, and
(c) 3-(4-morpholino)propylacrylate.

According to another preferred embodiment of the invention the copolymer consists of
(a) methylmethacrylate
(b) stearylmethacrylate and butylmethacrylate, and
(c) 2-(N',N'-dimethylamino)ethylmethacrylate
whereby the amount of stearylmethacrylate is at least 2 mol-%, the amount of butylmethacrylate is at least 5 mol-% and the amount of (c) is 22–28 mol-% of the amount of charged monomers.

According to another preferred embodiment of the invention the copolymer consists of
(a) methylmethacrylate
(b) stearylmethacrylate, and
(c) 2-(N',N'-dimethylamino)ethylmethacrylate
whereby the amount of (b) is 1 mol-%, and the amount of 2-(N',N'-dimethylamino)ethylmethacrylate is 22–28 mol-% of the amount of charged monomers.

The following copolymers were prepared by copolymerization of
(a) methylmethacrylate of the formula

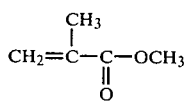

(b) at least one monomer of the general formula III

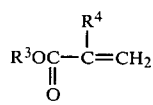

wherein $R^3$ is a straight and branched alkyl group having 4–18 C, and $R^4$ is hydrogen or methyl, and
(c) a monomer of the formula I

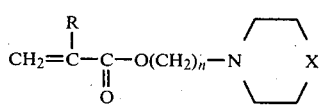 (I)

wherein R, X and n have the meanings given above and/or a monomer of the formula II

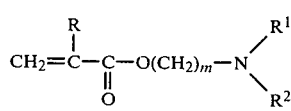 (II)

wherein R, $R^1$, $R^2$ and m have the meanings given above, together with a polymerization initiator, to the formation of the copolymer which is then isolated in a way known per se.

According to a preferred embodiment of the invention the monomers are added in accordance with the above given charges.

The polymerization can take place in any suitable solvent as benzene, cyclohexane, toluene, white spirit, hexane, xylene, as well as in a water emulsion.

The polymerization can further take place in a so called bulk-process, whereby the pure monomers are mixed and provided with a polymerization initiator. No other addition of the exemplified solvent, is carried out.

The polymerization can also take place in a suspension, whereby the monomers are suspended in a non-monomer-dissolving solvent, the initiator is added and the reaction takes place.

The polymerization can take place as a simple batch wise process where the components to be charged are added from the very beginning or in such a process that the most reactive monomer is added subsequently to its consumption. The latter gives a higher yield and an uniform composition of the product.

The polymerization is carried out at a temperature less than 100° C.

In order to initiate the polymerization an initiator can be added in the form of azobisisobutyronitrile (AIBN), sodium persulfate, peroxides, dimethylazobisisobutyrate. The amount of initiator can be varied but is generally 0.005–0.04 moles/mole of monomer mixture.

The present invention will be described more in detail in the following with reference to the examples below, however, without being restricted thereto.

EXAMPLE 1

2-(4-morpholino)ethylacrylate is prepared by adding 14.6 g of 2-(4-morpholino)ethanol dissolved in 52 mls of dry benzene to 11.4 g of acryloylchloride in 35 mls of dry benzene, whereby the monomers have been previously pured by distillation. Hereby white crystals of 2-(4-morpholino)ethylacrylate-hydrochloride are obtained, which were dissolved in water. After addition of sodium hydrogen-carbonate 2-(4-morpholino)ethylacrylate was extracted with chloroform and isolated by evaporation in vacuo. Hereby a yellowish oil was obtained having a density of 1.17. IR-analysis gave peaks at 1618, 1630 (the double bond), 1720 (the carbonyl group) and 2720–3000 cm$^{-1}$ (the morpholino group).

0.08 moles of 2-(4-morpholino)ethylacrylate were then copolymerized with 0.112 moles of methylmethacrylate and 0.008 moles of stearylmethacrylate according to the following.

14.8 g of 2-(4-morpholino)ethylacrylate, 11.2 g of methylmethacrylate and 2.59 g of stearylmethacrylate were charged in a retort containing 0.246 g of azobisisobutyronitrile (AIBN). The retort had prior to this been gassed with nitrogen gas before the polymerization was initiated. The components were dissolved in dry benzene (60 mls). Thereafter the temperature was raised to 60° C. and the polymerization started. During the polymerization reaction vigorous stirring took place. After 9 hours the solution thickened, whereby it was diluted with 50 mls of chloroform and was poured into petroleum ether, whereby the polymer precipitated. Dissolution in chloroform and precipitation in petroleum ether were repeated twice to give increased purity. The yield of copolymer was 52%. The polymer which has a softening point of 55° C. and contains 25 mol-% of 2-(4- morpholino)ethylacrylate, is completely soluble in an aqueous solution having a pH of 2 but only soluble to 3.7% in an aqueous solution of pH 5 after 24 hours. Molecular weight was determined to $\overline{Mn}=130,000$ and $\overline{Mw}=320,000$.

In accordance with Example 1 above the following polymers of the invention were prepared.

$Q_{35} = 551.1$ g · mil/m² · 24 hrs $Q_{39.5} = 435.6$ g · mil/m² · 24 hrs

1mil = 0.001 inches = 0.025m which give a Q mean value of 493 g.mil/m².24 hrs.

TABLE 1

| Polymer no | Monomer charged amount mol-% | | | | N-content % | $\overline{Mn}$ | $T_g$ °C. | $Q_{40}$ g · mil/m² · 24 hrs | Yield % |
|---|---|---|---|---|---|---|---|---|---|
| | MoEA | DEMA | MMA | SMA | | | | | |
| 031 | 40 | | 56 | 4 | 2.75 | 130,000 | — | 493 | 52 |
| 032 | 40 | | 50 | 10 | 2.3 | 114,000 | — | 276 | 50 |
| 033 | 40 | | 54 | 6 | 2.5 | 50,000 | — | 462 | 50 |
| 034 | 40 | | 57 | 3 | 2.7 | 120,000 | — | 539 | 52 |
| 036 | 40 | | 59 | 1 | 2.25 | 51,000 | 27 | 705 | 50 |
| 037 | 40 | | 56 | 4 | 2.35 | 100,000 | — | 427 | 50 |
| 039 | 40 | | 56 | 4 | 2.4 | 124,000 | — | 397 | 55 |
| 064 | 45 | | 54 | 1 | 2.93 | 36,000 | 33 | — | 63 |
| 065 | 45 | | 54 | 1 | 3.45 | — | — | 827 | 60 |
| 066 | 45 | | 54 | 1 | 3.55 | — | — | 669 | 60 |
| 067 | 45 | | 54 | 1 | 3.9 | — | — | 1562 | >70 |
| 068 | 45 | | 54 | 1 | 3.65 | — | — | 825 | 62 |
| 075 | 45 | | 54 | 1 | 3.25 | — | — | 528 | 61 |
| 077 | 45 | | 54 | 1 | 3.5 | — | — | 952 | 55 |
| 100 | 45 | | 54 | 1 | 2.25 | — | 35 | 739 | 60 |
| 101 | 45 | | 54 | 1 | 4.00 | — | 55 | 827 | 82 |
| 105 | 42.9 | | 56.1 | 1 | 3.5 | — | — | — | 30 |
| 106 | 46.2 | | 52.8 | 1 | 4.15 | — | — | — | 30 |
| 107 | 49.5 | | 49.5 | 1 | 7.0 | — | — | — | 10 |
| 108 | 52.8 | | 52.8 | 1 | 4.8 | — | — | — | 31 |
| 109 | 56.1 | | 56.1 | 1 | 2.9 | — | — | — | 30 |
| 110 | 35 | | 64 | 1 | 3.3 | — | — | — | 40 |
| 057 | 40 | | 59 | 1 | — | — | — | 690 | 71 |
| 058 | 40 | | 58 | 2 | — | — | — | 604 | 60 |
| 041 | 40 | | 56 | 4 | 2.2 | 190,000 | — | — | 50 |
| 050 | | 22 | 77 | 1 | 2.6 | — | — | 924 | 83 |
| 051 | | 24 | 75 | 1 | 2.9 | — | — | — | 76 |
| 055 | | 24 | 75 | 1 | 2.9 | — | 51 | 1198 | 73 |
| 060 | | 24 | 75 | 1 | 2.9 | — | 51 | 1062 | 83 |
| 070 | | 24 | 75 | 1 | 2.8 | — | — | 1237 | 82 |
| 071 | | 24 | 74 | 2 | 2.7 | — | — | 1002 | 77 |
| 072 | | 24 | 72 | 4 | 2.75 | — | — | 685 | 76 |
| 074 | | 24 | 66 | 10 | 2.44 | — | — | 540 | 64 |
| 102 | | 24 | 66 | 10 | 2.65 | — | 58 | 618 | 61 |
| 103 | | 24 | 66 | 10 | 2.15 | — | 54 | 670 | 92 |
| 104 | | 24 | 66 | 10 | 2.45 | — | 50 | 600 | 50 |

MoEA = 2-(4-morpholino)ethylacrylate
DEMA = 2-(N,N-dimethylamino)ethylmethacrylate
MMA = methylmethacrylate
SMA = stearylmethacrylate

TABLE 2

| Polymer no | Monomer charged amount mol-% | | | | N-content % | $\overline{Mn}$ | $T_g$ °C. | $Q_{40}$ g · mil/m² · 24 hrs | Yield % |
|---|---|---|---|---|---|---|---|---|---|
| | DEMA | MMA | SMA | BMA | | | | | |
| 81 | 24 | 52 | 4 | 20 | 2.6 | — | — | — | 82 |
| 82 | 24 | 62 | 4 | 10 | 2.7 | — | — | — | 78 |
| 83 | 24 | 67 | 4 | 5 | 2.65 | — | — | — | 75 |

BMA = butylmethacrylate

The copolymers prepared in accordance with above were tested with regard to watersteam permeability, whereby a film of the polymer having thickness of 0.07–0.10 mm was prepared. The film was applied close to an exicator containing $P_2O_5$, whereupon the exicator was placed in a box having controlled heating and was connected to a vacuum pump. The watersteam permeability Q was determined at two different temperatures by weighing the exicator prior to and after the process, whereby a very short through suction was carried out prior to the measuring in order to obtain a vacuum holding the film close to the edge. (Polymer 031).

The dissolution characteristics of the polymers obtained according to the invention were tested at different pH and in different solutions. Thereby tablets were tabletted containing glucose and lithium sulphate, respectively, and a colouring agent to give a rapid ocular control of the dissolution, whereupon the tablets were coated with a film according to the invention using a known coating technique. The tablets were then tested in a HCl-buffer pH 3, and in a buffer with pH 5, and/or synthetized rumen liquor pH 6.5 in a tablet disintegration apparatus. The results of these tests are given in Table below.

TABLE 3

| Polymer no | g polymer/100 g of tablets | Tablet contents | The solution was coloured yellow after min | | |
|---|---|---|---|---|---|
| | | | pH 3 | pH 5 | pH 6.5 |
| 031 | 2 | LiSO₄ | 25 | 40 | |
| 031 | 2 | Glucose | 20 | 35 | |
| 032 | 2 | LiSO₄ | 15 | 40 | |
| 032 | 2 | Glucose | 10 | 18 | |
| 033 | 2 | LiSO₄ | 13 | 40 | |
| 033 | 2 | Glucose | 9 | 25 | |
| 034 | 2 | LiSO₄ | 9 | 30 | |
| 034 | 2 | Glucose | 10 | 70 | |
| 036 | 2 | LiSO₄ | 10 | 60 | |
| 036 | 2 | Glucose | 17 | 60 | |
| 037 | 4 | LiSO₄ | 60 | >300 | |
| 037 | 4 | Glucose | >120 | >300 | |
| 037 | 8 | LiSO₄ | | | |
| 037 | 8 | Glucose | >120 | 240 | |
| 037 | 2 | LiSO₄ | 16 | 210 | |
| 037 | 2 | Glucose | 90 | 105 | |
| 039 | 2 | LiSO₄ | 40 | 160 | |
| 039 | 2 | Glucose | 30 | 40 | |
| 041 | 2 | LiSO₄ | 60 | >300 | |
| 041 | 2 | Glucose | 60 | 50 | |
| 050 | 2 | LiSO₄ | 7 | 50 | |
| 050 | 2 | Glucose | 4 | 60 | |
| 051 | 2 | LiSO₄ | 3 | 65 | |
| 051 | 2 | Glucose | 7 | 70 | |
| 051 | 4 | LiSO₄ | 10 | 240 | |
| 051 | 4 | Glucose | 25 | 120 | |
| 055 | 2 | LiSO₄ | 2 | 90 | |
| 057 | 2 | LiSO₄ | 2 | 60 | |
| 055 | 6 | LiSO₄ | 6 | | >300 |
| 055 | 6 | Glucose | 17 | | 270 |
| 057 | 6 | LiSO₄ | 5 | | >120 |
| 057 | 6 | Glocose | 30 | | 120 |
| 058 | 6 | LiSO₄ | >15 | | >300 |
| 060 | 4 | LiSO₄ | 3 | | 100 |
| 060 | 4 | Glucose | 3 | | 60 |
| 064 | 4 | LiSO₄ | 2 | | >300 |
| 064 | 4 | Glucose | 2 | | 105 |
| 064 | 6 | LiSO₄ | 9 | | >300 |
| 064 | 6 | Glucose | 2 | | >300 |
| 060 | 6 | LiSO₄ | 8 | | >255 |
| 060 | 6 | Glucose | 4 | | 75 |
| 031 | 4 | LiSO₄ | 13 | | >300 |
| 037 | 4 | LiSO₄ | 14 | | >300 |
| 041 | 4 | LiSO₄ | 25 | | >300 |
| 041 | 2 | LiSO₄ | 28 | | >300 |
| 070 | 4 | Glucose | 13 | | 150 |
| 070 | 6 | Glucose | 13 | | >300 |
| 071 | 4 | Glucose | 3 | | 60 |
| 071 | 6 | Glucose | 30 | | 180 |
| 072 | 4 | Glucose | 30 | | 120 |
| 072 | 6 | Glucose | 30 | | 120 |
| 074 | 4 | Glucose | 30 | | 120 |
| 074 | 6 | Glucose | 30 | | 120 |
| 075 | 4 | Glucose | 12 | | 180 |
| 075 | 6 | Glucose | 20 | | 180 |
| 077 | 4 | Glucose | 12 | | 40 |
| 077 | 6 | Glucose | 25 | | 70 |
| 100 | 6 | Glucose | 45 | | >300 |
| 101 | 6 | Glucose | 1 | | 120 |
| 102 | 6 | Glucose | 50 | | 560 |
| 103 | 6 | Glucose | 45 | | >300 |
| 104 | 6 | Glucose | 55 | | >300 |
| 100/067[x] | 6 | Glucose | 2 | | 45 |
| 100/101[xx] | 6 | Glucose | 27 | | >590 |

[x] 3 g + 3 g
[xx] 3.66 g + 2.34 g

The polymers prepared according to the invention and given in Table above were tested in a glycocoll-NaCl-HCl-buffer at different pH and in a physiological sodium chloride solution at different pH by addition of HCl. The results are given in Table 4 below.

Table 4

| Polymer no | Solubility in % | | | | | | | |
|---|---|---|---|---|---|---|---|---|
| | Buffer-solution | | | | Phys NaCl-solution | | | |
| | pH 2 | 3 | 4 | 5 | pH 2 | 3 | 4 | 5 |
| 081 | 30 | 12 | 11 | 3 | 21 | 0.4 | 3 | 0 |
| 082 | 94 | 31 | 10 | 0.5 | 98 | 30 | 5 | 0 |
| 083 | 94 | 28 | 0 | 0 | 99.5 | 31 | 0 | 0 |

EXAMPLE 2

A copolymer of 2-(N',N'-diethylamino)ethylmethacrylate, stearylmetacrylate, and methylmethacrylate was prepared by charging 0.048 mole of 2-(N',N'-diethylamino)ethylacrylate, 0.002 moles of stearylmethacrylate and 0.15 moles of methylmethacrylate in a retort containing 0.002 moles of AIBN. The retort had in accordance with Example 1 been gassed with nitrogen gas for half an hour before charging. The components were dissolved in dry benzene.

The polymers of the present invention are especially suitable for coating of particles intended for ruminants, whereby the object is to prevent a release in the rumen and thereby an attack by the microorganisms of the rumen, and instead provide for a release in the rennet stomach so that the animal can absorb the agent or agents, which the particles consist of or contain.

Substances, which can preferably be coated in this way are glucose, methionine, unsaturated fats, proteins, nutrient agents, and therapeutic agents.

Thus glucose is added to meet the great demand for glucose of high producing milk cows. Glucose is a source for production of lactose and a shortage thereof can lead to acetonemi and repugnance for feeding. The daily dose of glucose is 500–1000 g per animal.

Methionine is a first limiting amino acid in the production of proteins and in order to increase the biological value of the fodder supply methionine should preferably be added for this purpose. The daily dose of methionine is about 20 g per animal.

Unsaturated fat can be supplied in order to change the fatty acid composition of the milk and thereby of milk products, as butter and cheese, in order to thereby lower the blood fat ratio of the person having such milk or milk products. The daily dose of unsaturated fat is 500–1000 g per animal.

Particles containing such agents should have a particle size of 0.1–15 mm, preferably 0.2–3 mm in order to readily pass to the rumen without having been chewed. Particles should also have density of about 1 in order to pass on as soon as possible to the rest of the stomachs, because if they are too light they will only float around at the top in the rumen foam, while if they are too heavy they will sink to the bottom of the rumen and stay there for such a long time that release can take place notwithstanding. The density of the particles may easily be modified by means of e.g. kaolin.

The particles, in the form of pressed cores, granules, or the like, are coated with so much polymer material that a tight coating is obtained. This amount is as a rule 1 g of polymer per 100 g of particles.

The polymers are applied on the particles in a conventional coating apparatus, as coating pan or fluid bed, whereby the polymer dissolved in a suitable solvent as chloroform or methylenechloride is sprayed onto the particles.

We claim:

1. Product in the form of particles, which particles have been coated with a layer of polymer having pH dependent solubility characteristics in aqueous media, formed by the polymerization of
   (a) methylmethacrylate,
   (b) at least one monomer selected from the group consisting of a monomer of the general formula

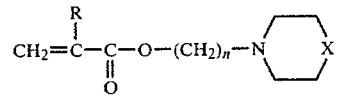

wherein R is selected from the group consisting of hydrogen and methyl, X is selected from the group consisting of —CH$_2$, and —O, and n is an integer of from 1–4, and a monomer of the general formula

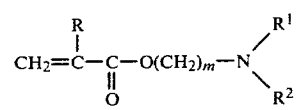

wherein R is selected from the group consisting of hydrogen and methyl, R$^1$ and R$^2$ are each selected from the group consisting of hydrogen, methyl, ethyl, propyl, isopropyl, isobutyl, t-butyl, and n-butyl, whereby R$^1$ and R$^2$ are not both hydrogen, and m is an integer of from 1–4; and wherein the monomer according to formula I, when present, is 30–50 mol-% of the amount of monomers charged; and wherein the monomer of formula II, when present, is 20–30 mol-% of the amount of monomers charged; and (c) at least one monomer of the general formula

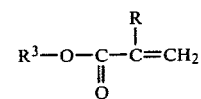

wherein R$^3$ is a straight or branched alkyl group having 4–18C, and R$^4$ is hydrogen or methyl, and wherein the monomer according to formula III is 0.5–6.0 mol-% of the amount of monomers charged; and wherein the polymer has pH dependent solubility such that the compound is essentially water insoluble above pH=5, but essentially water permeable at pH=3; and wherein the nitrogen content of the polymer is 2.5–3.3%.

2. Product according to claim 1 wherein said monomer III includes butylmethacrylate or stearylmethacrylate.

3. Method for the administration of products of the type of nutritional agents and therapeutic agents to the rennet stomach of a ruminant without causing an attack by the microorganisms of the rumen, whereby the product is provided with a polymer layer, which with regard to its solubility characteristics is pH dependent so that it is substantially soluble resistant at pH exceeding pH=5 and substantially soluble and/or provides for release of the coated agent at pH below pH 3, characterized in that the product has been coated with a polymer between
   (a) methylmethacrylate,
   (b) at least one monomer selected from the group consisting of a monomer of the general formula $$\underset{\substack{|\\ O}}{\overset{R}{CH_2=C-C}}-O-(CH_2)_n-N\diagup\diagdown X \qquad I$$

wherein R is selected from the group consisting of hydrogen and methyl, X is selected from the group consisting of —CH$_2$, and —O, and n is an integer of from 1–4, and monomer of the general formula $$\underset{\substack{\|\\O}}{\overset{R}{CH_2=C-C}}-O(CH_2)_m-N\diagup^{R^1}\diagdown_{R^2} \qquad II$$

wherein R is selected from the group consisting of hydrogen and methyl, R$^1$ and R$^2$ are each selected from the group consisting of hydrogen, methyl, ethyl, propyl, isopropyl, isobutyl, t-butyl, and n-butyl, whereby R$^1$ and R$^2$ are not both hydrogen, and m is an integer of from 1–4; and wherein the monomer according to formula I, when present, is 30–50 mol-% of the amount of monomers charged; and wherein the monomer of formula II, when present, is 20–30 mol-% of the amount of monomers charged; and (c) at least one monomer of the general formula $$R^3-O-\underset{\substack{\|\\O}}{\overset{R^4}{C}}-C=CH_2 \qquad III$$

wherein R$^3$ is a straight or branched alkyl group having 4–18C, and R$^4$ is hydrogen or methyl, and wherein the monomer according to formula III is 0.5–6.0 mol-% of the amount of monomer charged; and wherein the polymer has pH dependent solubility such that the compound is essentially water insoluble above pH=5, but essentially water permeable at pH=3; and wherein the nitrogen content of the polymer is 2.5–3.3%.

4. A polymer according to claim 3 wherein said monomer III includes butylmethacrylate or stearylmethacrylate.

5. Product according to claims 1 or 2, characterized in that it is a feedstuff for ruminants comprising a particle shaped, sugar-containing material.

6. Product according to claims 1 or 2, characterized in that it is a feedstuff for ruminants comprising a particle shaped, protein-containing material.

7. Product according to claims 1 or 2, characterized in that it is a feedstuff for ruminants comprising a particle shaped, amino acid containing material.

8. Product according to claims 1 or 2, characterized in that it is a feedstuff for ruminants comprising a particle shaped, unsaturated fat containing material.

9. Product according to claims 1 or 2, characterized in that it is a food stuff comprising a particle shaped, nutrient agent containing material.

10. Product according to claims 1 or 2, characterized in that it is a therapeutically active preparation comprising a particle shaped, therapeutic agent containing material.

11. Product according to one of claims 1 or 2 or 5–10, characterized in that the particles have been coated with a polymer between
    (a) methylmethacrylate
    (b) stearylmethacrylate, and
    (c) 2-(4-morpholino)ethylacrylate.

12. Product according to one of claims 1 or 2 or 5–10, characterized in that the particles have been coated with a polymer between
    (a) methylmethacrylate
    (b) stearylmethacrylate, and
    (c) 2-(N',N'-dimethylamino) ethylmethacrylate.

13. Product according to claim 12, characterized in that the polymer further comprises butylmethacrylate.

14. Product according to one of claims 1 or 2 or 5–10, characterized in that the particles present have a size of 0.1–15 mm and a density of about 1.

15. Product according to one of claims 1 or 2 or 5–10, characterized in that the particles have been coated with the polymer in an amount of at least 1.0 g per 100 g of particles.

* * * * *

UNITED STATES PATENT AND TRADEMARK OFFICE
CERTIFICATE OF CORRECTION

PATENT NO. : 4,234,565
DATED : Nov. 18, 1980
INVENTOR(S) : Flodin et al.

It is certified that error appears in the above—identified patent and that said Letters Patent is hereby corrected as shown below:

First page, Item 75, after "Djursholm" insert --Stig G. Widell, Kjulsta--. Col. 1, line 7, "filmcoating" should read --film coating--; line 31, after "monomer" insert a comma. Col. 2, line 14, after "integer" insert --of from--; same line, after "preferably" insert --from--. Col. 7, line 35, " >120" should read -- <120--; line 37, " >15    >300" should read -- <15    <300--; line 44, " >255" should read --255--. Col. 9, line 4, "stearylmetacrylate" should read --stearyl-methacrylate--; line 59, "methylenechloride" should read --methylene chloride--.

Signed and Sealed this

Seventeenth Day of August 1982

[SEAL]

Attest:

GERALD J. MOSSINGHOFF

*Attesting Officer*    *Commissioner of Patents and Trademarks*